United States Patent [19]

Oine et al.

[11] Patent Number: 4,727,071

[45] Date of Patent: * Feb. 23, 1988

[54] CEPHALOSPORIN COMPOUNDS

[75] Inventors: Toyonari Oine; Hiroshi Sugano, both of Nara; Yoshihisa Yamada, Kyoto; Totaro Yamaguchi, Urawa; Satoshi Ohshima, Iwatsuki, all of Japan

[73] Assignee: Tanabe Seiyaku Co., Ltd., Osaka, Japan

[*] Notice: The portion of the term of this patent subsequent to Jul. 1, 2003 has been disclaimed.

[21] Appl. No.: 835,886

[22] Filed: Mar. 4, 1986

Related U.S. Application Data

[62] Division of Ser. No. 516,053, Jul. 21, 1983, Pat. No. 4,598,075.

[30] Foreign Application Priority Data

Aug. 7, 1982 [GB] United Kingdom ............... 8222823

[51] Int. Cl.$^4$ ............... C07D 499/44; A61K 31/545
[52] U.S. Cl. ............................. 514/206; 540/225
[58] Field of Search ......................... 514/206; 540/225

[56] References Cited

U.S. PATENT DOCUMENTS 4,547,494 10/1985 Oine et al. ..................... 514/204
4,598,075 7/1986 Oine et al. ..................... 544/25
4,598,154 7/1986 Oine et al. ..................... 544/25

*Primary Examiner*—Nicholas S. Rizzo
*Attorney, Agent, or Firm*—Birch, Stewart, Kolasch & Birch

[57] ABSTRACT

A cephalosporin compound of the formula:

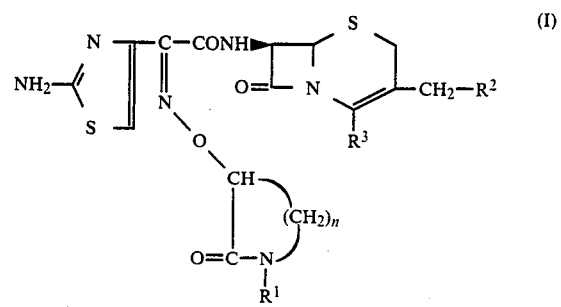

wherein
$R^1$ is hydrogen or lower alkyl;
$R^2$ is acetoxy or (1-methyl-1H-tetrazol-5-yl)thio, and
$R^3$ is carboxy; or
$R^2$ is a group of the formula:

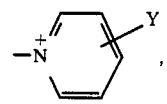

$R^3$ is —COO$^-$ and
Y is hydrogen, hydroxymethyl or carbamoyl; and
n is an integer of 2 or 3, or a pharmaceutically acceptable salt thereof and processes for their preparation are disclosed. Said cephalosporin compound is useful as an antimicrobial agent.

10 Claims, No Drawings

CEPHALOSPORIN COMPOUNDS

This application is a divisional of copending application Ser. No. 516,053, filed on July 21, 1983, now U.S. Pat. No. 4,598,075.

This invention relates to a novel cephalosporin compound and processes for preparing the same. More particularly, it relates to a compound of the formula:

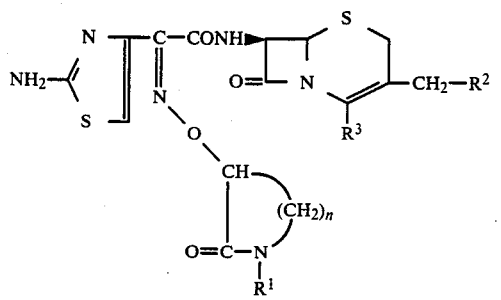
(I)

wherein
$R^1$ is hydrogen or lower alkyl;
$R^2$ is acetoxy or (1-methyl-1H-tetrazol-5-yl)thio, and $R^3$ is carboxy; or
$R^2$ is a group of the formula

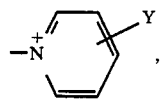

$R^3$ is $—COO^-$
and Y is hydrogen, hydroxymethyl or carbamoyl; and
n is an integer of 2 or 3, or a pharmaceutically acceptable salt thereof. A pharmaceutical composition for use as an antimicrobial agent which comprises the cephalosporin compound (I) or a salt thereof as an active ingredient together with an inert carrier therefor is also provided in the present invention.

The new cephalosporin compound (I) of the present invention and a pharmaceutical salt thereof show potent antimicrobial activity against a wide variety of microorganisms including gram-positive and gram-negative bacteria and are useful as anti-bacterial agents, as nutritional supplements in animal food or as chemotherapeutic agents in warm-blooded animals, including man, in the treatment of infectious diseases caused by said gram-positive and gram-negative bacteria.

Among the compounds of the present invention, a preferred subgenus includes those of the formula (I) in which $R^1$ is hydrogen, lower alkyl such as methyl, ethyl or propyl; $R^2$ is acetoxy or (1-methyl-1H-tetrazol-5-yl)thio, and $R^3$ is carboxy; or $R^2$ is a group of the formula:

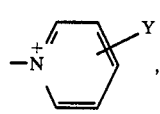

$R^3$ is $—COO^-$ and Y is hydrogen, hydroxymethyl or carbamoyl; and n is an integer of 2 or 3. A more preferred subgenus includes those of the formula (I) in which $R^1$ is hydrogen or methyl, $R^2$ is (1-methyl-1H-tetrazol-5-yl)thio, and $R^3$ is carboxy; or $R^2$ is a group of the formula:

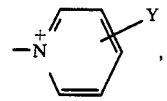

$R^3$ is $—COO^-$ and Y is hydrogen, 4-hydroxymethyl, 3-hydroxymethyl or 4-carbamoyl; and n is an integer of 2 or 3. A further preferred subgenus are those of the formula (I) in which $R^1$ is hydrogen, $R^2$ is a group of the formula:

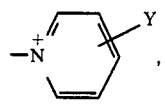

$R^3$ is $—COO^-$, Y is hydrogen and n is the integer of 2. The most preferred compound is the levorotatory isomer of the compound (I) in which $R^1$ is hydrogen, $R^2$ is a group of the formula:

$R^3$ is $—COO^-$, Y is hydrogen and n is the integer of 2. In addition, the structural formula (I) shown above is intended to show that the isomeric configuration of the oxyimino group is the Z (i.e., syn)-configuration. Although the Z (i.e., syn)-isomers of the invention are preferred and show the best biological properties, they may coexist with small amounts of the E (or anti)-isomer which may exist due to isomerization during the chemical preparation.

According to the present invention, the cephalosporin compound (I) is prepared by the steps of
(i) condensing a compound of the formula:

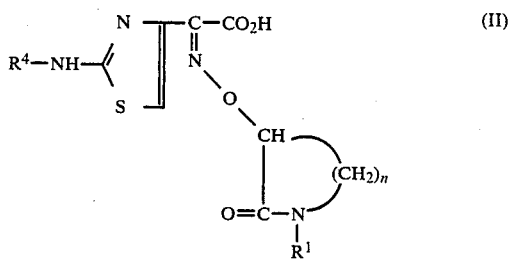
(II)

wherein $R^4$ is a protecting group and $R^1$ and n are the same as defined above, or a reactive derivative thereof with a compound of the formula:

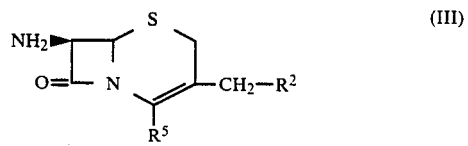
(III)

wherein $R^5$ is carboxy or a protected carboxy when $R^2$ is acetoxy or (1-methyl-1H-tetrazol-5-yl)thio; or $R^5$ is —COO⁻ when $R^2$ is a group of the formula:

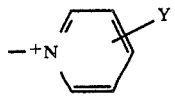

(Y is the same as defined above), or a salt thereof to give a compound of the formula:

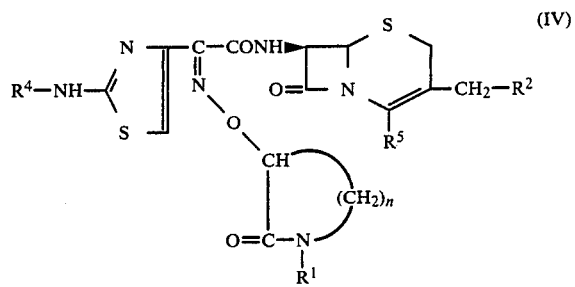

wherein $R^1$, $R^2$, $R^4$, $R^5$ and n are the same as defined above, and (ii) removing the protecting group or groups therefrom. Alternatively, the cephalosporin compound of the formula:

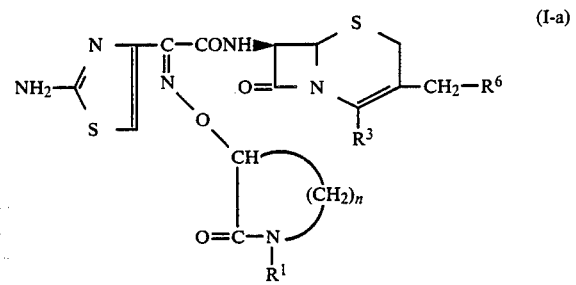

wherein $R^6$ is (1-methyl-1H-tetrazol-5-yl)thio or a group of the formula:

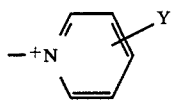

and $R^1$, $R^3$, Y and n are the same as defined above, is prepared by the steps of (i) reacting a compound of the formula:

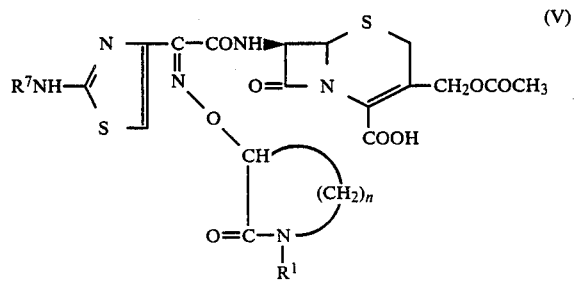

wherein $R^7$ is hydrogen or a protecting group and $R^1$ and n are the same as defined above, or a salt thereof with a pyridine compound of the formula:

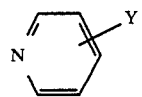

(Y is the same as defined above), (1-methyl-5-mercapto)tetrazol or a salt thereof, and (ii) when $R^7$ is a protecting group, further removing said protecting group therefrom.

In the above-mentioned reactions, a wide variety of protecting groups which have been usually employed to protect a amino group in the peptide synthesis can be used as the protecting group $R^4$ or $R^7$. Examples of such protecting groups include lower alkanoyl such as formyl, acetyl and pivaloyl; mono-, di- or trihalogeno-lower alkanoyl such as chloroacetyl and trifluoroacetyl; lower alkoxycarbonyl such as methoxycarbonyl, ethoxycarbonyl and tert.-butoxycarbonyl; substituted or unsubstituted benzyloxycarbonyl such as benzyloxycarbonyl and p-methoxybenzyloxycarbonyl; substituted or unsubstituted phenyl-lower alkyl such as p-methoxybenzyl and 3,4-dimethoxy-benzyl; and di- or triphenyl lower alkyl such as benzhydryl and trityl. On the other hand, when $R^5$ in the compound (III) or (IV) is a protected carboxy, the protecting group on the carboxy group should be one which can be easily removed by a conventional manner such as hydrolysis, acid treatment or reduction. Examples of such protecting groups include lower alkyl such as methyl, ethyl or tert.-butyl; substituted or unsubstituted phenyl-lower alkyl such as benzyl, p-methoxybenzyl and p-nitrobenzyl; benzhydryl; tri-lower alkylsilyl such as trimethylsilyl; and the like. When $R^5$ is carboxy, it is preferred that the compound (III) is converted to a salt thereof prior to carrying out the condensation reaction. Suitable examples of the salt of each one of the compound (III), the compound (V) and (1-methyl-5-mercapto)tetrazole are inorganic salts such as sodium or potassium salts or organic salts such as trimethylamine or triethylamine salts. Moreover, while the compound (II) can exist in the form of two optical isomers due to the asymmetric carbon atom involved in the group of the formula:

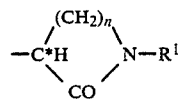

(wherein the asterisk denotes an asymmetric carbon atom), either an optical isomer of the compound (II) or a racemic modification thereof may be used for the purpose of the present invention. Throughout the specification and claims, "levorotatory isomer" of the compound (I), (II), (IV) or (V) in which $R^1$ is hydrogen and n is an integer of 2 means that the absolute configuration of said compound at said asymmetric carbon atoms is the S-configuration and also "dextrorotatory isomer" means that the absolute configuration of said compound at said asymmetric carbon atom is the R-configuration.

The condensation reaction of the compound (II) or a reactive derivative thereof with the compound (III) or a salt thereof can be accomplished in a conventional manner. For example, the condensation of the compound (II) in its free form with the compound (III) is conducted in the presence of a dehydrating agent in a solvent. Suitable examples of the dehydrating agent include dicyclohexylcarbodiimide, N-cyclohexyl-N'-morpholinocarbodiimide, N-ethyl-N'-(3-dimethylaminopropyl)-carbodiimide, phosphorus oxychloride, phosphorus trichloride, thionyl chloride, oxalyl chloride, triphenylphosphine and the like. Vilsmeier reagent prepared from dimethylformamide and phosphorus oxychloride, from dimethylformamide and oxalyl chloride, from dimethylformamide and phosgene or from dimethylformamide and thionyl chloride may also be used as said dehydrating agent. It is preferred to carry out the reaction at a temperature of −50° to 50° C., especially −30° to 20° C. Dioxane, tetrahydrofuran, acetonitrile, chloroform, methylene chloride, dimethylformamide, N,N-dimethylacetamide, ethyl acetate, pyridine, acetone and water are suitable as the solvent.

On the other hand, the condensation reaction of the reactive derivative of the compound (II) with the compound (III) or a salt thereof can be conducted either in the presence or absence of an acid acceptor in a solvent. Suitable examples of the reactive derivative of the compound (II) include the corresponding acid halides (e.g., chloride, bromide), mixed anhydrides (e.g., a mixed anhydride of the compound (II) with alkyl carbonate), active esters (e.g., p-nitrophenyl ester, 2,4-dinitrophenyl ester, succinimide ester, phthalimide ester, benzotriazole ester, 2-pyrrolidon-1-yl ester), acid azide and acid amides (e.g., imidazole amide, 4-substituted-imidazole amide, triazole amide). Dioxane, tetrahydrofuran, acetonitrile, chloroform, methylene chloride, dimethylformamide, N,N-dimethylacetamide, ethyl acetate, pyridine, acetone and water are suitable as the solvent. Moreover, suitable examples of the acid acceptor include alkali metal hydroxides (e.g., potassium hydroxide, sodium hydroxide), alkali metal carbonates or bicarbonates (e.g., sodium carbonate, sodium bicarbonate, potassium carbonate, potassium bicarbonate), trialkyl amines (e.g., trimethylamine, triethylamine), N,N-dialkylanilines (e.g., N,N-dimethylaniline, N,N-diethylaniline), pyridine and N-alkyl-morpholines (e.g., N-methylmorpholine). It is preferred to carry out the reaction at a temperature of −50° to 50° C., especially at −30° to 20° C.

The removal of the protecting group or groups from the compound (IV) thus obtained can be conducted by a conventional manner such as, for example, hydrolysis, solvolysis, acid treatment or reduction. For example, when the protecting group $R^4$ is formyl, acetyl, tert.-butoxycarbonyl, benzhydryl or trityl and the protecting group on the carboxy group is tert.-butyl or benzhydryl, said group or groups may be removed by treating the compound (IV) with an acid. Suitable examples of such acid include, for example, formic acid, trifluoroacetic acid, benzenesulfonic acid, p-toluene-sulfonic acid, hydrochloric acid or hydrogen bromide, especially trifluoroacetic acid. This reaction may be conducted with or without a solvent. Examples of the solvent are water, methanol, ethanol, acetic acid or dioxane. It is preferred to carry out the reaction at a temperature of −30° to 70° C., especially 0° to 30° C. Moreover, when the trifluoroacetic acid is used as the acid, it is preferred to carry it out in the presence of anisole. When the protecting group $R^4$ is benzyloxycarbonyl, p-methoxybenzyloxycarbonyl, benzyl, p-methoxy-benzyl or 3,4-dimethoxybenzyl and the protecting group on the carboxy group is benzyl, p-methoxybenzyl or p-nitrobenzyl, the removal of said protecting group or groups may be conducted by catalytic hydrogenation of the compound (IV) in hydrogen gas in the presence of a catalyst. This catalytic hydrogenation is preferably carried out at a temperature of 0° to 100° C., especially 10° to 40° C., under atmospheric or increased pressure. Preferred examples of the catalyst include palladium-$BaCO_3$, palladium-charcoal and palladium-black. Methanol, ethanol, tetrahydrofuran and water are suitable as the reaction solvent. Further, when the protecting group $R^4$ is trifluoroacetyl, pivaloyl, methoxycarbonyl or ethoxy-carbonyl and the protecting group on the carboxy group is methyl or ethyl, said group or groups may be removed by hydrolysis of the compound (IV). The hydrolysis of the compound (IV) can be carried out in a conventional manner, for example, by treating it with an alkali agent such as sodium hydroxide or potassium hydroxide, or an acid such as hydrochloric acid or hydrobromic acid. It is preferred to carry out said hydrolysis at a temperature of 0° to 70° C., especially 10° to 30° C. When the protecting group $R^4$ is chloroacetyl, said group may be removed by treating the compound (IV) with thiourea in a solvent. Methanol, ethanol and water are suitable as the solvent. It is preferred to carry it out at a temperature of 20° to 80° C., especially 40° to 80° C.

On the other hand, the reaction of the compound (V) or a salt thereof with the pyridine compound

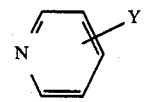

or (1-methyl-5-mercapto)-tetrazole or a salt thereof can be readily conducted in a solvent. Water, dimethylformamide and N,N-dimethylacetamide are suitable as the solvent. It is preferred to carry out the reaction at a temperature of 0° to 100° C., especially 20° to 80° C. It is also preferred to carry it out in the presence of sodium iodide, potassium iodide, sodium bicarbonate or phosphate buffer solution. Removal of the protecting group $R^7$ of the product thus obtained can be conducted in the same manner as in removing the protecting group or groups from the compound (IV).

Concomitantly, the starting compound (II) of the present invention is prepared, for example, by reacting a compound of the formula:

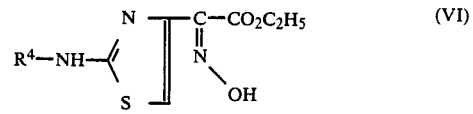

(VI)

wherein $R^4$ is the same as defined above, with a compound of the formula:

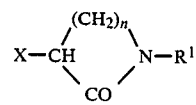

(wherein X is halogen and $R^1$ and n are the same as defined above) in the presence of an alkali agent (e.g., potassium carbonate) in a solvent (e.g., dimethylsulfoxide) at a temperature of 10° to 50° C. to give a compound of the formula:

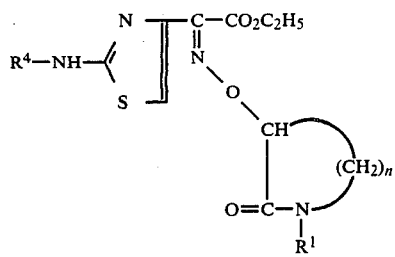

wherein $R^1$, $R^4$ are n are the same as defined above, and then hydrolyzing the compound (VII). Alternatively, the starting compound (II) may be prepared by hydrolyzing the compound (VI) to give a compound of the formula:

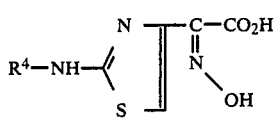

wherein $R^4$ is the same as defined above, and then reacting the compound (VIII) with a compound of the formula:

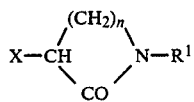

(wherein $R^1$, n and X are the same as defined above) in the presence of an acid acceptor (e.g., sodium hydride) at a temperature of 10° to 40° C. in a solvent (e.g., dimethylsulfoxide). Moreover, as mentioned hereinbefore, the compound (II) involves two optical isomers due to the asymmetric carbon involved in the group of the formula:

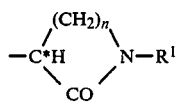

(wherein the asterisk denotes an asymmetric carbon atom). If required, however, such optical isomers may be separated into each of the optical isomers by optical resolution thereof. For example, the compound (II) in which $R^1$ is hydrogen, n is an integer of 2 and $R^4$ is trityl can be readily separated into each of the optical isomers by reacting the racemic modification of the compound (II) with L- or D-phenylalanine methyl ester in a solvent (e.g., a mixture of methanol and dioxane) to form the diastereoisomeric salts thereof, and separating said diastereoisomers into each component thereof by selective recrystallization. By said selective recrystallization, the least soluble diastereoisomer is recovered as crystals from the reaction mixture and the more soluble diastereoisomer remains soluble therein. It is preferred to carry out said selective crystallization at a temperature of 10° to 40° C.

The cephalosporin compound (I) of the present invention and pharmaceutically acceptable salts thereof show potent antimicrobial activity against a wide variety of microorganisms including those belonging to the genera Streptococcus (e.g., *St. faecalis, St. pneumoniae*), Staphylococcus (e.g., *S. aureus, S. epidermidis*) and Pseudomonas (e.g., *Ps. aeruginosa, Ps. putida, Ps. stutzeri*), and are particularly characterized by their potent antimicrobial activity against both gram-positive and gram-negative bacteria. For example, 7β-{(Z)-2-(2-aminothiazol-4-yl)-2-[(2-pyrrolidon-3-yl)oxyimino]acetamido}-3-(1-pyridiniomethyl)-3-cephem-4-carboxylate (l-isomer) and 7β-{(Z)-2-(2-aminothiazol-4-yl)-2-[(1-methyl-2-pyrrolidon-3-yl)oxyimino]acetamido}-3-[(1-methyl-1H-tetrazol-5-yl)thiomethyl]-3-cephem-4-carboxylic acid exhibit minimum inhibitory concentration (M.I.C.) (Agar dilution method, cultured for 20 hours at 37° C.) of 12.5 and 25 μg/ml against *Streptococcus faecalis* CN 478, while the M.I.C. of Cefmenoxime [Chemical name: 7β-[(Z)-2-(2-aminothiazol-4-yl)-2-(methoxyimino)acetamido]-3-[(1-methyl-1H-tetrazol-5-yl)thiomethyl]-3-cephem-4-carboxylic acid] and Ceftazidime [Chemical name: 7β-[(Z)-2-(2-aminothiazol-4-yl)-2-(2-carboxyprop-2-yloxyimino)acetamido]-3-(1-pyridiniomethyl)-3-cephem-4-carboxylate] against said microorganism are more than 100 μg/ml. The antimicrobial activity of 7β-{(Z)-2-(2-aminothiazol-4-yl)-2-[(2-pyrrolidon-3-yl)oxyimino]acetamido}-3-[(1-methyl-1H-tetrazol-5-yl)thiomethyl]-3-cephem-4-carboxylic acid against *Staphylococcus aureus* 252R is also more than 16 times stronger than those of Cefmenoxime and Ceftazidime. Moreover, the compound (I) and a salt thereof show potent antimicrobial activity against bacteria belonging to the genera Bacillus (e.g., *B. subtilis*), Escherichia (e.g., *E. coli*), Klebsiella (e.g., *K. pneumoniae*), Enterobacter (e.g., *E. aerogenes, E. cloacae*) and Serratia (e.g., *S. marcescens*).

The cephalosporin comound (I) may further exhibit potent antimicrobial activity against other bacteria belonging to the genera Citrobacter, Proteus, Shigella, Hemophilus and Salmonella. Further, the cephlasporin compound (I) and salts thereof are characterized in that they show potent protective effects against microbial infections of various bacteria including both *Staphylococcus aureus* and *Pseudomonas aeruginosa*, because of the high absorbability or long-lasting therapeutic effects in living tissues; that they have a high stability against a variety of β-lactamase-producing microorganisms, especially against β-lactamases produced by *Proteus vulgaris*; and also that they are low in toxicity. For example, no rats die even after 7β-{(Z)-2-(2-aminothiazol-4-yl)-2-[(2-pyrrolidon-3-yl)oxyimino]acetamido}-3-(1-pyridiniomethyl)-3-cephem-4-carboxylate (l-isomer) is administered subcutaneously to SD-male rats at a dose of 1000 mg for 14 consecutive days.

The cephalosporin compound (I) of the present invention can be used for pharmaceutical use either in the free form or in the form of a salt thereof. Pharmaceutically acceptable salts of the compound (I) include, for example, non-toxic metallic salts such as sodium, potassium, calcium or aluminum salts; ammonium salt; salts thereof with non-toxic amines such as trialkylamines (e.g., triethylamine and procaine); salts thereof with inorganic acids such as hydrochloric acid or hydrobromic acid; salts thereof with organic acids such as oxalic acid or tartaric acid; and so forth. These salts are easily obtained by treating the compound (I) with a stoichiometrically equi-molar amount of the corresponding alkali agent or acid at around room temperature in an aqueous solvent. The cephalosporin compound (I) and a salt thereof can be administered either orally or parenterally (e.g., intravenously, intramuscularly, subcutaneously). The daily dose of the compound (I) of a salt thereof may vary over a wide range depending on the age, weight or conditions of patients, and the severity of diseases to be treated. In general, however, a preferred daily dose of said compound (I) or a salt thereof may be about 0.002 to about 0.2 g, especially 0.01 to 0.04 g, per kg of body weight per day. Further, the compound (I) and a salt thereof may be used in the form of a pharmaceutical preparation containing the same compound in conjunction or admixture with pharmaceutical excipients suitable for oral or parenteral administration. Suitable excipients include, for example, gelatin, lactose, glucose, sodium chloride, starch, magnesium stearate, talcum, vegetable oil and other known medicinal excipients. The pharmaceutical preparations may be in solid form such as tablets, coated tablets, pills or capsules; or in liquid form such as solutions, suspensions or emulsions. They may be sterilized and/or may further contain auxiliaries such as stabilizing, wetting or emulsifying agents.

Practical and presently-preferred embodiments of the present invention are illustratively shown in the following Examples. Throughout the specification and claims, the term "lower alkyl" should be interpreted as referring to alkyl having one to four carbon atoms.

Experiment I (Antimicrobial activity in vitro)

The minimum inhibitory concentration (MIC, $\mu g/ml$) of a test compound was determined by means of a standard agar plate dilution method (based on the standard method of Japan Society of Chemotherapy). Media used in these experiments were Mueller-Hinton agar (MGA; Nissui).

The results are shown in the following Table 1.

TABLE 1

| Microorganisms tested | M.I.C. ($\mu g/ml$) | | |
|---|---|---|---|
| | The compound of the present invention (Note: 1) | Cefmenoxime (Note: 2) | Ceftazidime (Note: 3) |
| Staphylococcus aureus Terajima | 0.78 | 1.56 | 12.5 |
| Staphylococcus aureus 252R | 25 | >100 | >100 |
| Streptococcus faecalis CN-478 | 12.5 | >100 | >100 |
| Bacillus subtilis ATCC 6633 | 0.2 | 1.56 | 3.13 |
| Klebsiella pneumoniae 5038 | 0.05 | 0.1 | 0.1 |
| Enterobacter cloacae TU-680 | ≦0.05 | 0.1 | 0.2 |
| Serratia marcescens 7006 | ≦0.05 | 0.2 | 0.2 |
| Pseudomonas aeruginosa 4096 | 0.39 | 6.25 | 0.78 |
| Pseudomonas putida | 1.56 | 100 | 12.5 |

TABLE 1-continued

| Microorganisms tested | M.I.C. ($\mu g/ml$) | | |
|---|---|---|---|
| | The compound of the present invention (Note: 1) | Cefmenoxime (Note: 2) | Ceftazidime (Note: 3) |
| ATCC 12633 | | | |

Note:
(1): 7β-{(Z)—2-(2-aminothiazol-4-yl)-2-[(2-pyrrolidon-3-yl)-oxyimino]acetamido}-3-(1-pyridiniomethyl)-3-cephem-4-carboxylate (l-isomer)
(2): Chemical name = 7β-[(Z)—2-(2-aminothiazol-4-yl)-2-methoxyimino)acetamido]-3-[(1-methyl-1H—tetrazol-5-yl)-thiomethyl]-3-cephem-4-carboxylic acid
(3): Chemical name = 7β-[(Z)—2-(2-aminothiazol-4-yl)-2-(2-carboxy-prop-2-yloxyimino)acetamido]-3-(1-pyridiniomethyl)-3-cephem-4-carboxylate Experiment II (Protective effects on bacterial infections in mice)

Ten male mice weighing 20±1 g were used for each dose level. Mice were challenged via the intraperitoneal route with sufficient bacteria to kill all non-treated mice within 24 hours. All bacteria were suspended in 6% mucin. A test compound were administered intramuscularly one hour after the infection. Survival ratios were determined 7 days after the infection. The median effective doses ($ED_{50}$, mg/kg) of the test compound were estimated by the probito analysis.

The results are shown in the following Table 2 together with the M.I.C. ($\mu g/ml$) of the test compound which was estimated in the same manner as described in Experiment I.

TABLE 2*

| Microorganisms tested | $ED_{50}$ (mg/kg) | | |
|---|---|---|---|
| | The compound of the present invention (Note: 1) | Cefmenoxime (Note: 2) | Ceftazidime (Note: 3) |
| Staphylococcus aureus Smith | 1.71 (1.56) | 5.32 (1.56) | 7.85 (12.5) |
| Escherichia coli KC-14 | 0.05 (0.05) | 0.16 (0.025) | 0.08 (0.05) |
| Serratia marcescens 7006 | 0.14 (0.05) | 0.88 (0.2) | 0.54 (0.2) |
| Citrobacter freundii 916 | 0.06 (0.1) | 0.19 (0.05) | 0.15 (0.39) |
| Enterobacter aerogenes 816 | 1.37 (0.39) | 23.85 (1.56) | 26.38 (6.25) |

Note:
*the numerical values in parenthesises show the M.I.C. (minimum inhibitory concentration, $\mu g/ml$) of each test compound.
(1)–(3): same as shown in the footnote of Table 1.

EXAMPLE 1

(1) 3.2 g of (Z)-2-(2-tritylaminothiazol-4-yl)-2-[(2-pyrrolidon-3-yl)oxyimino]acetic acid are suspended in 60 ml of tetrahydrofuran, and 2.05 g of tert.-butyl 7-aminocephalosporanate, 1.27 g of 1-hydroxybenzotriazole and 1.93 g of dicyclohexylcarbodiimide are added thereto. The mixture is stirred at room temperature for 3 hours. Insoluble materials are filtered off, and the filtrate is concentrated to dryness under reduced pressure. The residue is dissolved in ethyl acetate, and the solution is washed with 1% hydrochloric acid, 5% aqueous sodium bicarbonate solution and water, successively. The ethyl acetate solution is dried and concentrated to dryness under reduced pressure. Then, the residue thus obtained is purified by silica gel chromatography (solvent, chloroform:methanol=98.5:1.5). 4.3 g of tert.-butyl 7β-{(Z)-2-(2-tritylaminothiazol-4-yl)-2-[(2-pyrrolidon-3-yl)oxyimino]acetamido}cephalosporanate are obtained as pale yellow powder.

M.p. 135°-145° C. (decomp.)

NMR (CDCl₃)δ: 1.52 (9H, s), 2.02 (3H, s), 2.2–2.7 (2H, m), 3.0–3.5 (4H, m), 4.5–5.3 (4H, m), 5.6–6.0 (1H, m), 6.70 (1H, s), 6.9–7.5 (17H, m), 8.4–8.7 (1H, broad).

(2) 1.0 g of tert.-butyl 7β-{(Z)-2-(2-tritylaminothiazol-4-yl)-2-[(2-pyrrolidon-3-yl)oxyimino]acetamido}cephalosporanate is added to a mixture of 20 ml of trifluoroacetic acid and one ml of anisole, and the mixture is stirred at room temperature for 20 minutes. The mixture is concentrated under reduced pressure to remove trifluoroacetic acid. Ether is added to the residue, and the resulting powder is collected by filtration. The powder is suspended in 10 ml of water and sodium bicarbonate is added thereto to dissolve said powder therein. The solution is washed with ethyl acetate and chromatographed on a column of non-ionic polymer resin Amberlite XAD-2 (registered trade mark, manufactured by Rohm & Haas Co. U.S.A.), using water as an eluent. The fractions containing the cephalosporin compound are collected and concentrated under reduced pressure to remove solvent. Then, acetone is added to the residue obtained, and the resulting powder is collected by filtration. 320 mg of sodium 7β-{(Z)-2-(2-aminothiazol-4-yl)-2-[(2-pyrrolidon-3-yl)oxyimino]acetamido}cephalosporanate are obtained as colorless powder.

NMR (D₂O)δ: 2.10 (3H, s), 2.2–2.7 (2H, m), 3.15–3.85 (4H, m), 4.6–5.00 (2H, m), 5.01 (1H, t, J=7 Hz), 5.16 (1H, d, J=5 Hz), 5.77 (1H, d, J=5 Hz), 6.98 (1H, s).

EXAMPLE 2

(1) 4.0 g of (Z)-2-(2-tritylaminothiazol-4-yl)-2-[(2-pyrrolidon-3-yl)oxyimino]acetic acid are dissolved in a mixture of 30 ml of tetrahydrofuran and 10 ml of N,N-dimethylacetamide, and 1.27 g of 1-hydroxybenzotriazole and 1.93 g of dicyclohexylcarbodiimide are added thereto. After the mixture is stirred at 0° to 5° C. for 2 hours, said mixture is added to 30 ml of N,N-dimethylacetamide-water (water content: 15%) containing 2.12 g of 7-aminocephalosporanic acid and 4 g of triethylamine. Said addition is carried out under ice-cooling. Then, the mixture is stirred at the same temperature for 1.5 hours. Insoluble materials are filtered off, and the filtrate is concentrated under reduced pressure to remove solvent. The residue is poured into 300 ml of water. Said mixture is adjusted to pH 8 with sodium bicarbonate, washed with ethyl acetate, adjusted to pH 3 with 2N hydrochloric acid, and then extracted wth ethyl acetate. The extract is dried and concentrated to dryness under reduced pressure. Ether is added to the residue thus obtained, and the resulting powder is collected by filtration. 3.1 g of 7β-{(Z)-2-(2-tritylaminothiazol-4-yl)-2-[(2-pyrrolidon-3-yl)oxyimino]acetamido}cephalosporanic acid are obtained.

NMR (DMSO-d₆)δ: 2.03 (3H, s), 2.1–2.5 (2H, m), 3.0–3.7 (4H, m), 4.4–5.2 (4H, m), 5.5–5.9 (1H, m), 6.71 (1H, s), 7.0–7.6 (15H, m), 7.84 (1H, s), 8.80 (1H, broad s), 9.50 (1H, broad d).

(2) 40 ml of 80% aqueous formic acid are added to 3.0 g of 7β-{(Z)-2-(2-tritylaminothiazol-4-yl)-2-[(2-pyrrolidon-3-yl)oxyimino]acetamido}-cephalosporanic acid, and the mixture is stirred at room temperature for 2 hours. Insoluble materials are filtered off, and the filtrate is concentrated to dryness under reduced pressure. Water is added to the residue, and the aqueous mixture is neutralized with sodium bicarbonate and washed with ether. Then, said aqueous mixture is chromatographed on a column of non-ionic polymer resin Diaion HP-20 (registered trade mark, manufactured by Mitsubishi Chemical Industries Ltd., Japan), using water as an eluent. The fractions containing the cephalosporin compound are collected and concentrated to dryness under reduced pressure. 1.5 g of sodium 7β-{(Z)-2-(2-aminothiazol-4-yl)-2-[(2-pyrrolidon-3-yl)oxyimino]acetamido}-cephalosporanate are obtained.

The physico-chemical properties of this product are identical with those of the sample obtained in Example 1-(2).

EXAMPLE 3

(1) 3.25 g of (Z)-2-(2-tritylaminothiazol-4-yl)-2-[(2-pyrrolidon-3-yl)oxyimino]acetic acid are dissolved in 200 ml of tetrahydrofuran, and 3.14 g of benzhydryl 7β-amino-3-[(1-methyl-1H-tetrazol-5-yl)thiomethyl]-3-cephem-4-carboxylate, 1.03 g of 1-hydroxybenzotriazole and 1.57 g of dicyclohexylcarbodiimide are added thereto. The mixture is stirred at room temperature for 2 hours. Insoluble materials are filtered off, and the filtrate is concentrated to dryness under reduced pressure. The residue is dissolved in ethyl acetate, and washed with 1% hydrochloric acid, 5% aqueous sodium bicarbonate solution and an aqueous saturated sodium chloride solution, successively. The ethyl acetate solution is then dried and concentrated to dryness under reduced pressure. The residue thus obtained is purified by silica gel chromatography (solvent, ethyl acetate:benzene=5:2). 3.7 g of benzhydryl 7β-{(Z)-2-(2-tritylaminothiazol-4-yl)-2-[(2-pyrrolidon-3-yl)oxyimino]acetamido}-3-[(1-methyl-1H-tetrazol-5-yl)thiomethyl]-3-cephem-4-carboxylate are obtained.

M.p. 122°-126° C. (decomp.)

NMR (CDCl₃)δ: 2.2–2.7 (2H, m), 3.0–3.5 (2H, m), 3.6–3.75 (2H, m), 3.78 (3H, s), 4.2–4.4 (2H, m), 5.03 (2H, m), 5.7–6.05 (1H, m), 6.75 (1H, s), 6.88 (1H, s), 7.1–7.5 (27H, m), 8.80 (1H, broad).

(2) 860 mg of benzhydryl 7β-{(Z)-2-(2-tritylaminothiazol-4-yl)-2-[(2-pyrrolidon-3-yl)oxyimino]acetamido}-3-[(1-methyl-1H-tetrazol-5-yl)thiomethyl]-3-cephem-4-carboxylate are added to a mixture of 10 ml of trifluoroacetic acid and 0.5 ml of anisole, and the mixture is stirred at room temperature for 20 minutes. The mixture is concentrated under reduced pressure to remove trifluoroacetic acid. Ether is added to the residue, and the resulting powder is collected by filtration. The powder is suspended in water, and sodium bicarbonate is added thereto to dissolve said powder therein. The solution is washed with ethyl acetate and chromatographed on a column of non-ionic polymer resin Amberlite XAD-2 (registered trade mark, manufactured by Rohm & Haas Co., U.S.A.), using water as an eluent. The fractions containing the cephalosporin compound are collected and concentrated to dryness under reduced pressure. 0.3 g of sodium 7β-{(Z)-2-(2-aminothiazol-4-yl)-2-[(2-pyrrolidon-3-yl)oxyimino]acetamido}-3-[(1-methyl-1H-tetrazol-5-yl)thiomethyl]-3-cephem-4-carboxylate is obtained.

NMR (DMSO-d₆)δ: 2.1–2.5 (2H, m), 3.1–3.5 (2H, m), 3.94 (3H, s), 4.2–4.5 (2H, m), 4.6–4.8 (1H, m), 5.03 (1H, d, J=5 Hz), 5.5–5.8 (1H, m), 6.76 (1H, s), 7.3 (2H, broad s), 8.00 (1H, s), 9.55 (1H, broad).

EXAMPLE 4

0.57 g of oxalyl chloride is added at −5° to 0° C. to 15 ml of chloroform containing 0.35 g of dimethylformamide, and the mixture is stirred at the same temperature for 15 minutes. A mixture of 1.54 g of (Z)-2-(2-tritylaminothiazol-4-yl)-2-[(2-pyrrolidon-3-yl)oxyimino]acetic acid, 0.3 g of triethylamine and 15 ml of chloroform is added to said mixture at −30° to −35° C., and the mixture is further stirred at the same temperature for 5 minutes. Then, a solution of 7β-amino-3-(1-pyridinio-methyl)-3-cephem-4-carboxylate in chloroform (said solution is prepared by suspending 1.82 g of the dihydrochloride of said cephem compound in 10 ml of chloroform and adding 4 ml of N,O-bis(trimethylsilyl)acetamide thereto to dissolve said salt therein) is added to said mixture at −35° to −30° C., and the mixture is stirred at the same temperature for 10 minutes and at −30° to −10° C. for one hour. The mixture is concentrated to dryness under reduced pressure. 60 ml of 80% aqueous formic acid are added to the residue, and the aqueous mixture is stirred at room temperature for one hour. 50 ml of water are added to said aqueous mixture. Then, insoluble materials are filtered off, and the filtrate is washed with ethyl acetate and concentrated to dryness under reduced pressure. The residue thus obtained is dissolved in water and chromatographed on a column of non-ionic polymer resin Diaion HP-20 (registered trade mark, manufactured by Mitsubishi Chemical Industries Ltd., Japan). The column is washed with water, followed by elution with 20% methanol. The fractions containing the cephalosporin compound are collected and concentrated to dryness under reduced pressure. Acetone is added to the residue thus obtained, and the resulting powder is collected by filtration. 0.84 g of 7β-{(Z)-2-(2-aminothiazol-4-yl)-2-[(2-pyrrolidon-3-yl)oxyimino]acetamido}-3-(1-pyridiniomethyl)-3-cephem-4-carboxylate is obtained.

M.p.>250° C.

NMR (D$_2$O)δ: 2.2–2.7 (2H, m), 3.1–3.7 (4H, m), 4.9–5.5 (4H, m), 5.80 (1H, d, J=5 Hz), 6.92 (1H, s), 7.8–9.1 (5H, m).

$[\alpha]_D^{20}$+13.4° (C=1.0, H$_2$O).

EXAMPLE 5

1.56 g of oxalyl chloride are added at −5° to 0° C. to 39 ml of chloroform containing 0.99 ml of dimethylformamide, and the mixture is stirred at the same temperature for 15 minutes. A solution of 4.23 g of (Z)-2-(2-tritylaminothiazol-4-yl)-2-[(2-pyrrolidon-3-yl)oxyimino]acetic acid (d-isomer) and 0.84 g of triethylamine in 39 ml of chloroform is added to said mixture at −30° C. The mixture is stirred at the same temperature for 5 minutes. Then, a solution of 7β-amino-3-(1-pyridiniomethyl)-3-cephem-4-carboxylate in chloroform (said solution is prepared by suspending 5.0 g of the dihydrochloride of said cephem compound in 39 ml of chloroform and adding 11 ml of N,O-bis(trimethylsilyl)acetamide thereto to dissolve said salt therein) is added to the said mixture at −30° to −10° C. After the mixture is stirred at the same temperature for 30 minutes, said mixture is concentrated to dryness under reduced pressure. 100 ml of 80% aqueous formic acid are added to the residue, and said aqueous mixture is stirred at room temperature for one hour. 100 ml of water are added to the mixture, and insoluble materials are filtered off. The filtrate is washed with ethyl acetate and is concentrated to dryness under reduced pressure. The residue thus obtained is dissolved in water and chromatographed on a column of non-ionic polymer resin Diaion HP-20 (resistered trade mark, manufactured by Mitsubishi Chemical Industries Ltd., Japan). The column is washed with water, followed by elution with 20% aqueous methanol. The fractions containing the cephalosporin compound are collected and concentrated to dryness under reduced pressure. Acetone is added to the residue, and the resulting powder is collected by filtration. 2.14 g of 7β-{(Z)-2-(2-aminothiazol-4-yl)-2-[(2-pyrrolidon-3-yl)oxyimino]acetamido}-3-(1-pyridiniomethyl)-3-cephem-4-carboxylate (d-isomer) are obtained. Another designation of this dextrorotatory isomer is shown as 7β-{(Z)-2-(2-aminothiazol-4-yl)-2-[((3R)-2-pyrrolidon-3-yl)oxyimino]acetamido}-3-(1-pyridiniomethyl)-3-cephem-4-carboxylate.

NMR (D$_2$O)δ: 2.1–2.7 (2H, m), 3.1–3.7 (4H, m), 4.9–5.5 (4H, m), 5.79 (1H, d, J=5 Hz), 6.92 (1H, s), 7.8–9.1 (5H, m).

$[\alpha]_D^{20}$+45.7° (C=1, H$_2$O).

EXAMPLE 6

1.81 g of oxalyl chloride are added at −5° to 0° C. to 45 ml of chloroform containing 1.15 ml of dimethylformamide, and the mixture is stirred at the same temperature for 15 minutes. A solution of 4.90 g of (Z)-2-(2-tritylaminothiazol-4-yl)-2-[(2-pyrrolidon-3-yl)oxyimino]acetic acid (l-isomer) and 0.97 g of triethylamine in 45 ml of chloroform is added to said mixture at −30° C. The mixture is stirred at the same temperature for 5 minutes. Then, a solution of 7β-amino-3-(1-pyridiniomethyl)-3-cephem-4-carboxylate in chloroform (said solution is prepared by suspending 5.8 g of the dihydrochloride of said cephem compound in 45 ml of chloroform and adding 12.7 ml of N,O-bis(trimethylsilyl)acetamide thereto to dissolve said salt therein) is added to the said mixture at −30° to −10° C. After the mixture is stirred at the same temperature for 30 minutes, said mixture is concentrated to dryness under reduced pressure. 100 ml of 80% aqueous formic acid are added to the residue, and said aqueous mixture is stirred at room temperature for one hour. 110 ml of water are added to the mixture, and insoluble materials are filtered off. The filtrate is washed with ethyl acetate and is concentrated to dryness under reduced pressure. The residue thus obtained is dissolved in water and chromatographed on a column of non-ionic polymer resin Diaion HP-20 (registered trade mark, manufactured by Mitsubishi Chemical Industries Ltd., Japan). The column is washed with water, followed by elution with 20% aqueous methanol. The fractions containing the cephalosporin compound are collected and concentrated to dryness under reduced pressure. Acetone is added to the residue, and the resulting powder is collected by filtration. 2.22 g of 7β-{(Z)-2-(2-aminothiazol-4-yl)-2-[(2-pyrrolidon-3-yl)oxyimino]acetamido}-3-(1-pyridiniomethyl)-3-cephem-4-carboxylate (l-isomer) are obtained. Another designation of this levorotatory isomer is shown as 7β-{(Z)-2-(2-aminothiazol-4-yl)-2-[((3S)-2-pyrrolidon-3-yl)oxyimino]acetamido}-3-(1-pyridiniomethyl)-3-cephem-4-carboxylate.

NMR (D$_2$O)δ: 2.2–2.7 (2H, m), 3.1–3.8 (4H, m), 5.05 (1H, t, J=7 Hz), 5.28 (1H, d, J=5 Hz), 5.36 (1H, d, J=14 Hz), 5.63 (1H, d, J=14 Hz), 5.87 (1H, d, J=5 Hz), 6,98 (1H,s), 8.10 (2H, t, J=7.5 Hz), 8.57 (1H, t, J=7.5 Hz), 8.98 (1H, d, J=7.5 Hz).

$[\alpha]_D^{20}$−38.0° (C=1, H$_2$O).

EXAMPLE 7

A mixture of 13 g of sodium iodide and 4 ml of water is stirred at 80° C. 3.6 g of pyridine and 3.2 g of 7β-{(Z)-2-(2-aminothiazol-4-yl)-2-[(2-pyrrolidon-3-yl)oxyimino]acetamido}cephalosporanic acid are added to said mixture, and the mixture is stirred at 75° to 80° C. for one hour. After cooling, the reaction mixture is poured into 150 ml of water and concentrated to dryness under reduced pressure. The residue is dissolved in 150 ml of water, and the solution is adjusted to pH 1 with 2N hydrochloric acid. Insoluble materials are filtered off, and the filtrate is washed with ethyl acetate, adjusted to pH 6 with 2N sodium hydroxide solution and concentrated to a total volume of 30 ml under reduced pressure. The solution thus obtained is chromatographed on a column of non-ionic polymer resin Diaion HP-20 (registered trade mark, manufactured by Mitsubishi Chemical Industries Ltd., Japan). The column is washed with water, followed by elution with 20% aqueous methanol. The fractions containing the cephalosporin compound are collected and concentrated to dryness under reduced pressure. Acetone is added to the residue thus obtained, and the resulting powder is collected by filtration. 0.67 g of 7β-{(Z)-2-(2-aminothiazol-4-yl)-2-[(2-pyrrolidon-3-yl)oxyimino]acetamido}-3-(1-pyridiniomethyl)-3-cephem-4-carboxylate is obtained.

The physico-chemical properties of the product are identical with those of the sample obtained in Example 4.

EXAMPLE 8

(1) 1.5 g of (Z)-2-(2-tritylaminothiazol-4yl)-2-[(1-methyl-2-pyrrolidon-3-yl)oxyimino]acetic acid are dissolved in 50 ml of tetrahydrofuran, and 1.4 g of benzhydryl 7β-amino-3-[(1-methyl-1H-tetrazol-5-yl)thiomethyl]-3-cephem-4-carboxylate, 0.6 g of 1-hydroxybenzotriazole and 0.92 g of dicyclohexylcarbodiimide are added thereto. The mixture is stirred at room temperature for 2 hours. Then, the reaction mixture is treated in the same manner as described in Example 3-(1). 1.58 g of benzhydryl 7β-{(Z)-2-(2-tritylaminothiazol-4-yl)-2-[(1-methyl-2-pyrrolidon-3-yl)oxyimino]acetamido}-3-[(1-methyl-1H-tetrazol-5-yl)thiomethyl]-3-cephem-4-carboxylate are obtained.

NMR (CDCl$_3$)δ: 2.2–2.6 (2H, m), 2.75 (3H, s), 3.1–3.5 (2H, m), 3.5–3.8 (2H, m), 3.84 (3H, s), 4.2–4.4 (2H, m), 4.8–5.2 (2H, m), 5.8–6.1 (1H, m), 6.72 (1H, s), 6.90 (1H, s), 7.0–7.5 (25H, m), 8.5–8.8 (2H, broad).

(2) 1.5 g of benzhydryl 7β-{(Z)-2-(2-tritylaminothiazol-4-yl)-2-[(1-methyl-2-pyrrolidon-3-yl)oxyimino]acetamido}-3-[(1-methyl-1H-tetrazol-5-yl)thiomethyl]-3-cephem-4-carboxylate are added to a mixture of 1.5 ml of anisole and 10 ml of trifluoroacetic acid, and the mixture is stirred at room temperature for 30 minutes. The mixture is concentrated under reduced pressure to remove trifluoroacetic acid. Ether is added to the residue, and the resulting powder is collected by filtration. The powder is suspended in 15 ml of water, and sodium bicarbonate is added thereto to dissolve said powder therein. The solution is washed with ethyl acetate and chromatographed on a column of non-ionic polymer resin Amberlite XAD-2 (registered trade mark, manufactured by Rohm & Haas Co., U.S.A.), using water as an eluent. The fractions containing the cephalosporin compound are collected and concentrated to dryness under reduced pressure. 0.61 g of sodium 7β-{(Z)-2-(2-aminothiazol-4-yl)-2-[(1-methyl-2-pyrrolidon-3-yl)oxyimino]acetamido}-3-[(1-methyl-1H-tetrazol-5-yl)thiomethyl]-3-cephem-4-carboxylate is obtained.

NMR (D$_2$O)δ: 2.1–2.7 (2H, m), 2.89 (3H, s), 3.2–3.8 (4H, m), 4.05 (3H, s), 4.05–4.3 (2H, m), 4.9–5.3 (2H, m), 5.73 (1H, d, J=5 Hz), 7.00 (1H, s).

EXAMPLE 9

(1) 0.5 g of (Z)-2-(2-tritylaminothiazol-4-yl)-2-[(2-piperidon-3-yl)oxyimino]acetic acid is dissolved in 10 ml of tetrahydrofuran, and 0.47 g of benzhydryl 7β-amino-3-[(1-methyl-1H-tetrazol-5-yl)thiomethyl]-3-cephem-4-carboxylate, 0.15 g of 1-hydroxybenzotriazole and 0.24 g of dicyclohexylcarbodiimide are added thereto. The mixture is stirred at room temperature for 2.5 hours. The reaction mixture is treated in the same manner as described in Example 3-(1). 0.47 g of benzhydryl 7β-{(Z)-2-(2-tritylaminothiazol-4-yl)-2-[(2-piperidon-3-yl)oxyimino]acetamido}-3-[(1-methyl-1H-tetrazol-5-yl)thiomethyl]-3-cephem-4-carboxylate is obtained.

NMR (DMSO-d$_6$)δ: 2.00–2.5 (4H, m), 3.0–3.3 (2H, m), 3.6–3.8 (2H, m), 3.8 (3H, s), 4.1–4.3 (2H, m), 4.6–4.8 (1H, m), 4.9–5.4 (1H, m), 5.85 (1H, d, d, J=8 Hz, J=5 Hz), 6.71 (1H, s), 6.81 (1H, s), 7.0–7.6 (26H, m), 9.63 (1H, d, J=9 Hz).

(2) 0.4 g of benzhydryl 7β-{(Z)-2-(2-tritylaminothiazol-4-yl)-2-[(2-piperidon-3-yl)oxyimino]acetamido}-3-[(1-methyl-1H-tetrazol-5-yl)thiomethyl]-3-cephem-4-carboxylate is added to a mixture of 1.0 ml of trifluoroacetic acid and 0.8 ml of anisole, and the mixture is allowed to stand at room temperature for 30 minutes. The mixture is evaporated under reduced pressure to remove trifluoroacetic acid. Ether is added to the residue, and the resulting powder is collected by filtration. The powder is suspended in water, and sodium bicarbonate is added thereto to dissolve said powder therein. The solution is washed with ethyl acetate and chromatographed on a column of non-ionic polymer resin Amberlite XAD-2 (registered trade mark, manufactured by Rohm & Haas Co., U.S.A.). The column is washed with water, followed by elution with 10% aqueous methanol. The fractions containing the cephalosporin compound are collected and concentrated to dryness under reduced pressure. 0.9 g of sodium 7β-{(Z)-2-(2-aminothiazol-4-yl)-2-[(2-piperidon-3-yl)oxyimino]acetamido}-3-[(1-methyl-1H-tetrazol-5-yl)thiomethyl}-3-cephem-4-carboxylate is obtained.

NMR (D$_2$O)δ: 1.5–2.3 (4H, m), 3.0–3.4 (2H, m), 3.4–3.6 (2H, m), 3.90 (3H, m), 4.0–4.2 (2H, m), 5.03 (1H, d, J=5 Hz), 5.63 (1H, d, J=5 Hz), 5.85 (1H, s).

EXAMPLE 10

(1) 18.2 g of phosphorus oxychloride are added dropwise to 9.2 ml of dimethylformamide under ice-cooling, and the mixture is stirred at 25° to 35° C. for 30 minutes. After cooling to 0° C., 100 ml of chloroform are added to the mixture, and said mixture is further cooled to −35° C. A solution of 20 g of (Z)-2-(2-tritylaminothiazol-4-yl)-2-[(2-pyrrolidon-3-yl)oxyimino]acetic acid (l-isomer) and 5.6 ml of triethylamine in 160 ml of N,N-dimethylacetamide is added dropwise to the mixture at −35° to −25° C., and the mixture is stirred at the same temperature for 20 minutes. Then, a solution of 7-aminocephalosporanic acid (said solution being prepared by stirring a mixture of 16 g of 7-aminocephalosporanic acid, 48 g of trimethyl chlorosilane, 35.6 ml of pyridine and 160 ml of N,N-dimethylacetamide at 10° to 20° C. for 2 hours) is added dropwise to the reaction mixture at −35° to −20° C. under stirring. After stirring at the same temperature for 20 minutes, said reaction mixture is poured into 2 liters of ice-water and stirred vigorously. Crystalline precipitates are collected by filtration, washed with water, ethyl acetate and ether, and then dried in vacuo. 26.5 g of 7β-{(Z)-2-(2-tritylaminothiazol-4-yl)-2-[(2-pyrrolidon-3-yl)oxyimino]acetamido}cephalosporanic acid (l-isomer) are obtained as colorless powder.

NMR (DMSO-$d_6$)δ: 2.06 (3H,s), 2.1–2.5 (2H, m), 3.1–3.4 (2H, m), 3.45 (1H, d, J=18 Hz), 3.75 (1H, d, J=18 Hz) 4.6–5.02 (3H, m), 5.17 (1H, d, J=5 Hz), 5.6–5.9 (1H, m), 6.81 (1H, s), 7.1–7.6 (15H, m), 7.97 (1H, s), 8.88 (1H, br, s), 9.64 (1H, d, J=6 Hz).

(2) 67.5 g of sodium iodide and 10.9 g of pyridine are added to a mixture of 18 ml of water and 18 ml of dimethylformamide, and the mixture is heated to 80° C. 11.5 g of 7β-{(Z)-2-(2-tritylaminothiazol-4-yl)-2-[(2-pyrrolidon-3-yl)oxyimino]acetamido}cephalosporanic acid (l-isomer) are added to the mixture. The mixture is stirred at 80° C. for 35 minutes. After cooling, 90 ml of ice-water are added to the reaction mixture, and said mixture is washed with ethyl acetate. Then, the reaction mixture is evaporated under reduced pressure to remove ethyl acetate and adjusted to pH 2 with 10% hydrochloric acid. Crystalline precipitates are collected by filtration, washed with water and dried in vacuo. 11.9 g of 7β-{(Z)-2-(2-tritylaminothiazol-4-yl)-2-[(2-pyrrolidon-3-yl)oxyimino]acetamido}-3-(1-pyridiniomethyl)-3-cephem-4-carboxylate (l-isomer) are obtained as crude pale yellow powder.

(3) 5.5 g of 7β-{(Z)-2-(2-tritylamino-thiazol-4-yl)-2-[(2-pyrrolidon-3-yl)oxyimino]acetamido}-3-(1-pyridiniomethyl)-3-cephem-4-carboxylate (l-isomer) obtained above are dissolved in 90 ml of 80% formic acid. The solution is stirred at room temperature for one hour. The reaction solution is concentrated under reduced pressure, and 200 ml of water are added to the residue. Insoluble materials are filtered off. The aqueous filtrate is washed with ethyl acetate, concentrated under reduced pressure to remove ethyl acetate and then introduced into a column packed with 200 ml of a non-ionic adsorption resin (manufactured by Mitsubishi Chemical Industries Ltd. under the trade name "Diaion HP-20"). After the column is washed with water, said column is eluted with 20% aqueous methanol. The eluate is concentrated under reduced pressure, acetone is added to the residue and the resultant precipitates are collected by filtration. 1.6 g of 7β-{(Z)-2-(2-aminothiazol-4-yl)-2-[(2-pyrrolidon-3-yl)oxyimino]acetamido}-3-(1-pyridiniomethyl)-3-cephem-4-carboxylate (l-isomer) are obtained as pale yellow powder.

The physicochemical properties of this product are identical with those of the sample obtained in Example 6.

EXAMPLE 11

2.5 g of 7β-}(Z)-2-(2-tritylamino-thiazol-4-yl)-2-[(2-pyrrolidon-3-yl)oxyimino]acetamido}cephalosporanic acid (l-isomer) obtained in the same manner as described in Example 10-(1) are dissolved in 50 ml of 80% formic acid, and the solution is stirred at room temperature for one hour. Insoluble materials are filtered off. The filtrate is concentrated under reduced pressure, water is added to the residue, and the aqueous mixture is neutralized with sodium bicarbonate. Then, said aqueous mixture is washed with ethyl acetate, concentrated under reduced pressure and introduced into a column packed with 200 ml of a non-ionic adsorption resin (37 Diaion HP-20"). After the column is washed with water, said column is treated in the same manner as described in Example 10-(3). 1.0 g of sodium 7β-{(Z)-2-(2-aminothiazol-4-yl)-2-[(2-pyrrolidon-3-yl)oxyimino]acetamido}cephalosporanate (l-isomer) is obtained as pale yellow powder. Another designation of this levorotatory isomer is shown as sodium 7β-{(Z)-2-(2-aminothiazol-4-yl)-2-[((3S)-2-pyrrolidon-3-yl)-oxyimino]acetamido}cephalosporanate.

NMR ($D_2O$)δ: 2.12 (3H,s), 2.3–2.6 (2H, m), 3.2–3.9 (4H, m), 4.75 (1H, d, J=13 Hz), 4.95 (1H, d, J=13 Hz), 5.10 (1H, t, J=7 Hz), 5.25 (1H, d, J=5 Hz), 5.85 (1H, d, J=5 Hz), 7.08 (1H, s).

The product obtained above is treated in the same manner as described in Example 7, whereby 7β-{(Z)-2-(2-aminothiazol-4-yl)-2-[(2-pyrrolidon-3-yl)oxyimino]acetamido}-3-(1-pyridiniomethyl)-3-cephem-4-carboxylate (l-isomer) is obtained.

EXAMPLE 12

A mixture of 960 mg of 7β-{(Z)-2-(2-aminothiazol-4-yl)-2-[(2-pyrrolidon-3-yl)oxyimino]acetamido}cephalosporanic acid, 730 mg of isonicotinamide, 4.5 g of sodium iodide and 3 ml of water is stirred at 65° to 70° C. for 6 hours. After cooling, 20 ml of water are added to the reaction mixture, and insoluble materials are filtered off. The filtrate is introduced into a column packed with 100 ml of a non-ionic adsorption resin ("Diaion HP-20"). The column is washed with water. Then, said column is eluted with 20% aqueous methanol, and the eluate is concentrated under reduced pressure. 175 mg of 7β-{(Z)-2-(2-aminothiazol-4-yl)-2-[(2-pyrrolidon-3-yl)-oxyimino]acetamido}-3-(4-carbamoyl-1-pyridiniomethyl)-3-cephem-4-carboxylate are obtained as pale yellow powder.

m.p. 163°–166° C. (decomp.)

NMR ($CF_3CO_2D$)δ: 2.5–3.0 (2H, m), 3.5–4.0 (4H, m), 5.2–5.5 (3H, m), 5.5–5.8 (1H, m), 5.9–6.2 (1H, m), 7.35 (1H, s), 8.4–8.7 (2H, m), 9.1–9.4 (2H, m).

EXAMPLE 13

A mixture of 960 mg of 7β-{(Z)-2-(2-aminothiazol-4-yl)-2-[(2-pyrrolidon-3-yl)oxyimino]acetamido}cephalosporanic acid, 650 mg of 4-hydroxymethylpyridine, 4.5 g of sodium iodide and 3 ml of water is stirred at 65° to 70° C. for 7 hours. Then, the reaction mixture is treated in the same manner as described in Example 12. 150 mg of 7β-{(Z)-2-(2-aminothiazol-4-yl)-2-[(2-pyrrolidon-3-yl)oxyimino]-acetamido}-3-(4-hydroxymethyl-1-pyridiniomethyl)-3-cephem-4-carboxylate are obtained as pale yellow powder.

m.p. 162°–184° C. (decomp.)

NMR ($D_2O$)δ: 2.3–2.7 (2H, m), 3.1–3.7 (4H, m), 4.8–5.0 (2H, m), 5.03 (2H, s), 5.24 (1H, d, J=5 Hz), 5.3–5.6 (1H, m), 5.83 (1H, d, J=5 Hz), 6.81 (1H, s), 7.8–8.2 (2H, m), 8.6–9.0 (2H, m).

EXAMPLE 14

A mixture of 960 mg of 7β-{(Z)-2-(2-aminothiazol-4-yl)-2-[(2-pyrrolidon-3-yl)oxyimino]acetamido}cephalosporanic acid, 650 mg of 3-hydroxymethylpyridine, 4.5 g of sodium iodide and 3 ml of water is treated in the same manner as described in Example 12. 83 mg of 7β-{(Z)-2-(2-aminothiazol-4-yl)-2-[(2-pyrrolidon-3- yl)oxyimino]-acetamido}-3-(3-hydroxymethyl-1-pyridiniomethyl)-3-cephem-4-carboxylate are obtained.

m.p. 128°–135° C. (decomp.)

NMR. (D₂O)δ: 2.1–2.8 (2H, m), 3.1–3.8 (4H, m), 4.86 (2H, s), 4.9–5.1 (2H, m), 5.27 (1H, d, J=5 Hz), 5.3–5.6 (1H, m), 5.83 (1H, d, J=5 Hz), 6.96 (1H, s), 7.7–8.2 (1H, m), 8.3–8.6 (1H, m), 8.6–9.1 (2H, m).

Preparation of Starting compounds:

(1) 15.8 g of ethyl (Z)-2-(2-tritylaminothiazol-4-yl)-2-hydroxyiminoacetate are dissolved in 70 ml of dimethylsulfoxide, and 5.8 g of anhydrous potassium carbonate are added thereto. The mixture is stirred at room temperature for 20 minutes. 6.6 g of 3-bromo-2-pyrrolidone are added to said mixture, and the mixture is stirred at room temperature for 20 hours. The mixture is poured into 800 ml of water, and crystalline precipitates are collected by filtration and washed with water. The crystals are dissolved in chloroform, washed with water and then dried. Then, the chloroform solution is evaporated under reduced pressure to remove solvent. 100 ml of ethyl acetate are added to the residue, and allowed to stand at room temperature. Crystalline precipitates thus obtained are collected by filtration and dried. 16.0 g of ethyl (Z)-2-(2-tritylaminothiazol-4-yl)-2-[(2-pyrrolidon-3-yl)oxyimino]acetate are obtained.

M.p. 209°–210° C.

NMR (CDCl₃)δ: 1.30 (3H, t, J=7 Hz), 2.1–2.6 (2H, m), 3.1–3.6 (2H, m), 4.34 (2H, q, J=7 Hz), 4.90 (1H, t, J=7 Hz), 6.53 (1H, s), 7.0–7.6 (17H, m).

16.0 g of ethyl (Z)-2-(2-tritylaminothiazol-4-yl)-2-[(2-pyrrolidon-3-yl)oxyimino]acetate are added to a mixture of 160 ml of methanol and 30 ml of an aqueous 2N sodium hydroxide solution, and the mixture is refluxed for 30 minutes under heating. After cooling, crystalline precipitates are collected by filtration and washed with methanol. The crystals are suspended in 30 ml of water. Then, the suspension is adjusted to pH 3 with 2N hydrochloric acid. Crystalline precipitates are collected by filtration and dried. 11.4 g of (Z)-2-(2-tritylaminothiazol-4-yl)-2-[(2-pyrrolidon-3-yl)oxyimino]acetic acid are obtained.

M.p. 150°–153° C. (decomp.)

NMR (DMSO-d₆)δ: 1.8–2.4 (2H, m), 2.9–3.4 (2H, m), 4.63 (1H, t, J=7 Hz), 6.76 (1H, s), 6.9–7.6 (15H, m), 7.85 (1H, s), 8.70 (1H, broad s).

(2) 30 g of (Z)-2-(2-tritylaminothiazol-4-yl)-2-[(2-pyrrolidon-3-yl)oxyimino]acetic acid and 60 ml of methanol are added to 100 ml of dioxane containing 10.5 g of methyl L-phenylalaninate, and the mixture is heated at 50° C. to dissolve said acid therein. 700 ml of dioxane are added to the solution, and the mixture is stirred at room temperature for 5 hours. Crystalline precipitates are collected by filtration (the filtrate is hereinafter referred to as "Filtrate I"), and 14.3 g of the crude product thus obtained are dissolved in 24 ml of methanol. 280 ml of dioxane are added to the methanol solution. The mixture is stirred at room temperature for 4 hours, and crystalline precipitates are collected by filtration (the filtrate is hereinafter referred to as "Filtrate II"). 12.2 g of (Z)-2-(2-tritylaminothiazol-4-yl)-2-[(2-pyrrolidon-3-yl)oxyimino]acetic acid (l-isomer) methyl L-phenylalaninate salt are obtained.

$[\alpha]_D^{25}$ −14.0° (C=1, methanol).

12.2 g of the above-mentioned salt are dissolved in 120 ml of methanol, and 176 ml of 0.1N hydrochloric acid are added thereto. The mixture is stirred for 2 hours under ice-cooling. Crystalline precipitates are collected by filtration and washed with methanol. 7.5 g of (Z)-2-(2-tritylaminothiazol-4-yl)-2-[(2-pyrrolidon-3-yl)oxyimino]acetic acid (l-isomer) are obtained. Another designation of this levorotatory isomer is shown as (Z)-2-(2-tritylaminothiazol-4-yl)-2-[((3S)-2-pyrrolidon-3-yl)oxyimino]acetic acid.

M.p. 142°–143° C. (decomp.).

$[\alpha]_D^{25}$ −38.8° (C=1, dimethylformamide).

(3) Filtrates I and II obtained in the above mentioned paragraph (2) are condensed to dryness under reduced pressure. The residue is dissolved in 250 ml of methanol and then 450 ml of 0.1N hydrochloric acid are added dropwise to the solution. The mixture is stirred for 2 hours under ice-cooling. The resulting crystalline precipitates are collected by filtration, washed with methanol, and dried. 20 g of (Z)-2-(2-tritylaminothiazol-4-yl)-2-[(2-pyrrolidon-3-yl)oxyimino]acetic acid (containing excess of the d-isomer) are obtained. 20.0 g of (Z)-2-(2-tritylaminothiazol-4-yl)-2-[(2-pyrrolidon-3-yl)oxyimino]acetic acid thus recovered and 40 ml of methanol are added to 70 ml of dioxane containing 7.0 g of methyl D-phenylalaninate, and the mixture is heated at 50° C. to dissolve said acid therein. 450 ml of dioxane are added to said solution. Then, the mixture is stirred at room temperature for 4 hours, and crystalline precipitates are collected by filtration. 13.3 g of the crude product thus obtained are dissolved in 20 ml of methanol, and 260 ml of dioxane are added thereto. The mixture is stirred at room temperature for 4 hours. Crystalline precipitates are collected by filtration. 12.0 g of (Z)-2-(2-tritylaminothiazol-4-yl)-2-[(2-pyrrolidon-3-yl)oxyimino]acetic acid (d-isomer) methyl D-phenylalaninate salt are obtained.

$[\alpha]_D^{25}$ +13.9° (C=1, methanol).

12.0 g of the above-mentioned salt are dissolved in 120 ml of methanol, and 174 ml of 0.1N hydrochloric acid are added thereto. The mixture is stirred for 2 hours under ice-cooling. Crystalline precipitates are collected by filtration and washed with methanol. 7.3 g of (Z)-2-(2-tritylaminothiazol-4-yl)-2-[(2-pyrrolidon-3-yl)oxyimino]acetic acid (d-isomer) are obtained. Another designation of this dextrorotatory isomer is shown as (Z)-2-(2-tritylaminothiazol-4-yl)-2-[((3R)-2-pyrrolidon-3-yl)oxyimino]acetic acid.

M.p. 143°–144° C. (decomp.).

$[\alpha]_D^{25}$ +37.4° (C=1, dimethylformamide).

(4) 2.7 g of ethyl (Z)-2-(2-tritylaminothiazol-4-yl)-2-hydroxyiminoacetate are dissolved in 12 ml of dimethylsulfoxide, and 1.0 g of anhydrous potassium carbonate is added thereto under nitrogen gas atmosphere. The mixture is stirred at room temperature for 10 minutes. 1.2 g of 1-methyl-3-bromo-2-pyrrolidone are added to the mixture, and the mixture is stirred at room temperature for 5 hours. The reaction mixture is poured into 100 ml of water, and crystalline precipitates are collected by filtration. The crystals are dissolved in ethyl acetate, and the solution is washed with water and then dried. The solution is concentrated under reduced pressure to remove solvent. Then, the residue is crystallized with isopropyl ether and collected by filtration. 2.1 g of ethyl (Z)-2-(2-tritylaminothiazol-4-yl)-2-[(1-methyl-2-pyrrolidon-3-yl)oxyimino]acetate are obtained.

NMR (CDCl₃)δ: 1.30 (3H, t, J=7 Hz), 2.0–2.7 (2H, m), 2.88 (3H, s), 3.0–3.6 (2H, m), 4.34 (2H, q, J=7 Hz), 4.92 (1H, t, J=7 Hz), 6.54 (1H, s), 6.87 (1H, s), 7.0–7.5 (15H, m).

2.7 g of ethyl (Z)-2-(2-tritylaminothiazol-4-yl)-2-[(1-methyl-2-pyrrolidon-3-yl)oxyimino]acetate are suspended in 27 ml of methanol, and 4.9 ml of 2N sodium hydroxide solution are added thereto. The mixture is refluxed for 20 minutes under heating. After cooling, the mixture is concentrated under reduced pressure to remove methanol. The residue is adjusted to pH 3 with 2N hydrochloric acid and extracted with ethyl acetate. The extract is dried and evaporated under reduced pressure to remove solvent. Then, the residue thus obtained is crystallized with ether and collected by filtration. 2.15 g of (Z)-2-(2-tritylaminothuazol-4-yl)-2-[(1-methyl-2-pyrrolidon-3-yl)oxyimino]acetic acid are obtained.

M.p. 142°–145° C. (decomp.).

NMR (DMSO-$d_6$)$\delta$: 2.0–2.5 (2H, m), 2.77 (3H, s), 3.1–3.4 (2H, m), 4.78 (1H, t, J=8 Hz), 6.87 (1H, s), 6.9–7.5 (16H, m).

(5) 1.3 g of (Z)-2-(2-tritylaminothiazol-4-yl)-2-hydroxyiminoacetic acid are dissolved in 10 ml of dimethylformamide, and 0.24 g of sodium hydride (60% oil dispersion) is added thereto. The mixture is stirred at room temperature for 15 minutes. 0.65 g of 3-bromo-2-piperidone is added to the mixture, and the mixture is stirred at room temperature for 1.5 hours. The reaction mixture is poured into water and washed with a mixture of ethyl acetate and tetrahydrofuran (1:1). The aqueous layer is adjusted to pH 3 with 10% hydrochloric acid and extracted with a mixture of ethyl acetate and tetrahydrofuran (1:1). The extract is dried and concentrated to dryness under reduced pressure. Then, ether is added to the residue, and the resulting powder is collected by filtration. The powder (1.3 g) is purified by silica gel chromatography (solvent, methanol:chloroform=1:4). 0.85 g of (Z)-2-(2-tritylaminothiazol-4-yl)-2-[(2-piperidon-3-yl)oxyimino]acetic acid are obtained.

M.p. 145°–150° C. (decomp.).

What we claim is:

1. A 7$\beta$-[(Z)-2-(2-aminothiazol-4-yl)-2-oxyimino-acetamido]-3-cephem-4-carboxylic acid compound of the formula:

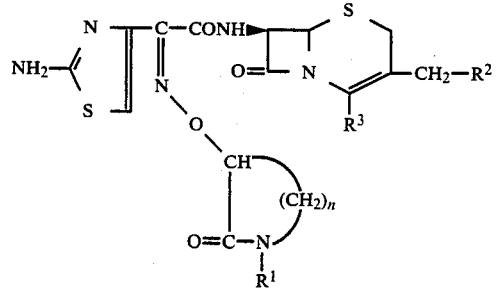

(I)

wherein
R$^1$ is hydrogen or lower alkyl;
R$^2$ is acetoxy or (1-methyl-1H-tetrazol-5-yl)thio, and R$^3$ is carboxy; or
R$^2$ is a group of the formula:

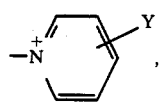

R$^3$ is —COO$^-$ and Y is hydrogen, hydroxymethyl or carbamoyl; and
n is an integer of 2 or 3,
or a pharmaceutically acceptable salt thereof.

2. The compound claimed in claim 1, in which R$^1$ is hydrogen or methyl; R$^2$ is acetoxy or (1-methyl-1H-tetrazol-5-yl)thio, and R$^3$ is carboxy; or R$^2$ is a group of the formula:

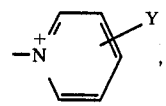

and R$^3$ is —COO$^-$ and Y is hydrogen, hydroxymethyl or carbamoyl; and n is an integer of 2 or 3.

3. The compound claimed in claim 1, in which R$^1$ is hydrogen or methyl; R$^2$ is (1-methyl-1H-tetrazol-5-yl)thio, and R$^3$ is carboxy; or R$^2$ is a group of the formula:

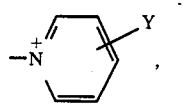

R$^3$ is —COO$^-$ and Y is hydrogen, 4-hydroxymethyl, 3-hydroxymethyl or 4-carbamoyl; and n is an integer of 2 or 3.

4. The compound claimed in claim 1, in which R$^1$ is hydrogen; R$^2$ is a group of the formula:

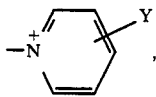

R$^3$ is —COO$^-$, and Y is hydrogen, 4-hydroxymethyl, 3-hydroxymethyl or 4-carbamoyl, and n is an integer of 2.

5. A pharmaceutical composition which comprises an antimicrobial effective amount of a 7$\beta$-[(Z)-2-(2-aminothiazol-4-yl)-2-oxyimino-acetamido]-3-cephem-4-carboxylic acid compound of the formula:

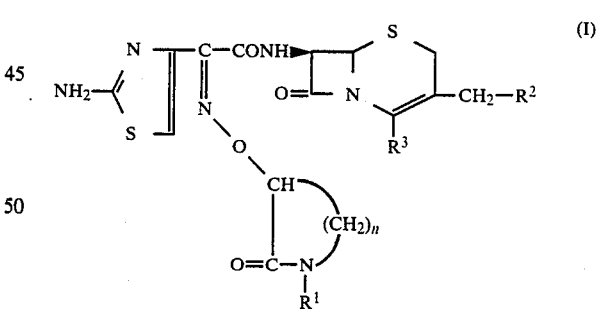

(I)

wherein
R$^1$ is hydrogen or lower alkyl;
R$^2$ is acetoxy or (1-methyl-1H-tetrazol-5-yl)thio and R$^3$ is carboxy; or
R$^2$ is a group of the formula:

R$^3$ is —COO$^-$ and Y is hydrogen, hydroxymethyl or carbamoyl; and n is an integer of 2 or 3, or a pharmaceutically acceptable salt thereof and a pharmaceutically acceptable carrier therefor.

6. The pharmaceutical composition claimed in claim 5, wherein said cephalosporin compound is a compound of the formula (I) in which R¹ is hydrogen,
R² is a group of the formula:

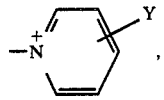

R³ is —COO⁻,
Y is hydrogen, 4-hydroxymethyl, 3-hydroxymethyl or 4-carbamoyl and n is an integer of 2.

7. A method of treating microbial infections in a warm-blooded animal comprising administering to said warm-blooded animal an antimicrobial effective amount of a 7β-[(Z)-2-(2-aminothiazol-4-yl)-2-oxyimino-acetamido]-3-cephem-4-carboxylic acid compound of the formula:

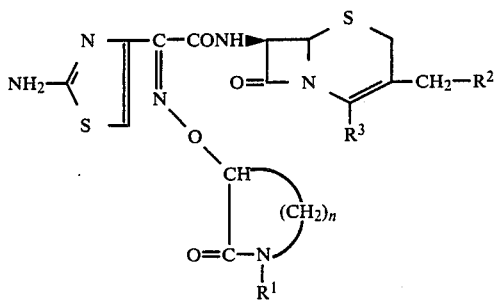

(I)

wherein

R¹ is hydrogen or lower alkyl;
R² is acetoxy or (1-methyl-1H-tetrazol-5-yl)thio and
R³ is carboxy; or
R² is a group of the formula:

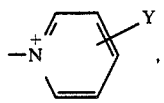

R³ is —COO⁻ and Y is hydrogen, hydroxymethyl or carbamoyl; and n is an integer of 2 or 3,
or a pharmaceutically acceptable salt thereof.

8. The method claimed in claim 7, wherein said cephalosporin compound is a compound of the formula (I) in which R¹ is hydrogen, R² is a group of the formula:

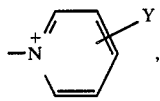

R³ is —COO⁻, Y is hydrogen, 4-hydroxymethyl, 3-hydroxymethyl or 4-carbamoyl, and
n is an integer of 2.

9. The method claimed in claim 7, wherein said cephalosporin compound is 7β-{(Z)-2-(2-aminothiazol-4-yl)-2-[(2-pyrrolidon-3-yl)oxyimino]acetamido}-3-(1-pyridiniomethyl)-3-cephem-4-carboxylate or a pharmaceutically acceptable salt thereof.

10. The method claimed in claim 7, wherein said cephalosporin compound is 7β-{(Z)-2-(2-aminothiazol-4-yl)-2-[((3S)-2-pyrrolidon-3-yl)oxyimino]acetamido}-3-(1-pyridiniomethyl)-3-cephem-4-carboxylate or a pharmaceutically acceptable salt thereof.

* * * * *